United States Patent [19]
Piot et al.

[11] Patent Number: 5,624,795
[45] Date of Patent: Apr. 29, 1997

[54] ISOLATION AND CHARACTERIZATION OF A NOVEL CHIMPANZEE LENTIVIRUS, DESIGNATED SIMIAN IMMUNODEFICIENCY VIRUS ISOLATE CPZ-ANT

[75] Inventors: Peter Piot, Berchem; Guido Van Der Groen, Kontich; Eric DeLaporte; Martine Peeters, both of Antwerp, all of Belgium

[73] Assignee: Innogenetics, N.V., Belgium

[21] Appl. No.: 955,894

[22] PCT Filed: Jun. 14, 1991

[86] PCT No.: PCT/EP91/01108

§ 371 Date: Feb. 11, 1993

§ 102(e) Date: Feb. 11, 1993

[87] PCT Pub. No.: WO91/19785

PCT Pub. Date: Dec. 26, 1991

[30] Foreign Application Priority Data

Jun. 15, 1990 [EP] European Pat. Off. ............... 90111364

[51] Int. Cl.$^6$ ............... G01N 33/53; C12N 7/00; C12N 7/01; A61K 39/21
[52] U.S. Cl. ............... 435/5; 435/235.1; 424/188.1; 424/208.1
[58] Field of Search ............... 435/5, 7.1, 6, 240.26, 435/240.27, 320.1, 975; 530/350, 395, 388.1, 388.35; 436/513, 514, 547, 548; 424/187.1, 188.1, 204.1, 207.1, 208.1; 935/3, 6, 22, 55, 65, 89

[56] References Cited

PUBLICATIONS

Huet et al: "Genetic organization of a chimpanzee lentivirus related to HIV–1" *Nature* vl. 345 356–359 24 May 1990.
Peeters et al: "Isolation and partial characterization of an HIV–related virus occurring naturally in chimpanzees in Gabon" *AIDS* vol. 3 No. 10 pp. 625–630 (1989).
Peeters et al., 1990, v Intl. Conf. AIDS p. 598, Abstract W.C.P. 40.
Huet et al., 1990, Nature 345:356–359.
Peeters et al., 1989, AIDS 3:625–630.

*Primary Examiner*—Christine M. Nucker
*Assistant Examiner*—Jeffrey S. Parkin
*Attorney, Agent, or Firm*—Banner & Witcoff, Ltd.

[57] ABSTRACT

The present invention relates to a retrovirus isolated from a chimpanzee and designated as SIV$_{cpz-ant}$ and to variants of this virus, having the following essential morphological and immunological properties: the virus exhibits a tropism for T4 lymphocytes, the virus does not exhibit cytopathic effect with the formation of giant cells in the lymphocytes that it infects, the virus has a diameter of approximately 130 nm, the virus possesses a magnesium dependent reverse transcriptase activity, it can be cultivated in T4 receptor-bearing immortalized cell-lines, lysates of the virus containing a p27 protein that is immunologically distinct from the p25 of HIV-1 and p19 protein of HTLV-1 on Western Blot, lysates of the virus containing a gp140 protein which is immunologically distinct from the gp120 of HIV-1 and gp140 of HTLV-1 by Western Blot analysis, the lysate of the virus contains an additional transmembrane glycoprotein with a molecular weight of 44,000 to 50,000 kD.

9 Claims, 7 Drawing Sheets

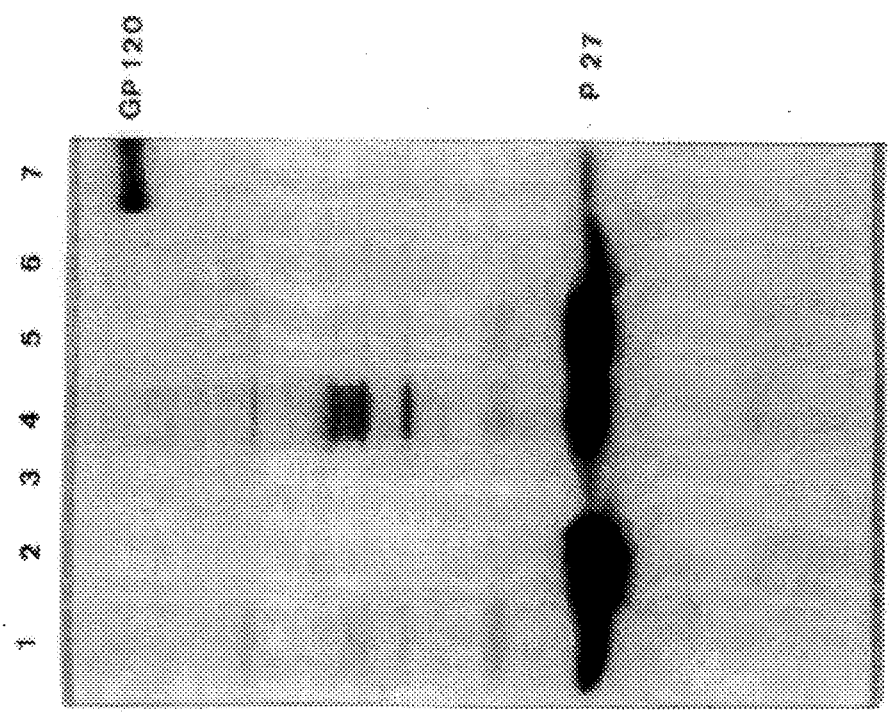
FIG. 6b SIV mnd
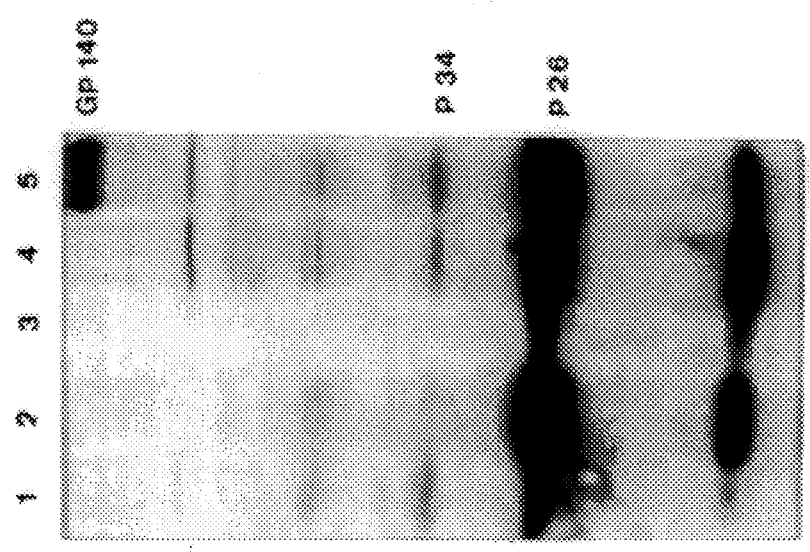
FIG. 6a HIV 2

SIVcpz ant

ISOLATION AND CHARACTERIZATION OF A NOVEL CHIMPANZEE LENTIVIRUS, DESIGNATED SIMIAN IMMUNODEFICIENCY VIRUS ISOLATE CPZ-ANT

This application was filed under 35 U.S.C. § 371 based upon PCT application EP91/01108, filed Jun. 14, 1991.

Substantial progress has been made in our understanding of the acquired immunodeficiency syndrome or AIDS. The principal causative agent has been demonstrated to be a non-transforming retrovirus with a tropism for T4 helper/inducer lymphocytes (1, 2) and it has been estimated that millions of people world-wide have already been infected. Infection with this virus leads, at least in a significant percentage of cases, to a progressive depletion of the T4 lymphocyte population with a concomitant increasing susceptibility to the opportunistic infections which are characteristic of the disease.

Epidemiological studies indicate that human immunodeficiency virus, type 1 (H1V-1), the etiological agent responsible for the majority of AIDS cases, is currently the most widely disseminated HIV and is predominant in Central Africa, Europe and the U.S.A.

A second group of human immunodeficiency-associated retroviruses, human immunodeficiency virus type 2 (HIV-2), was identified in West Africa (3, 4). An HIV-2 virus is disclosed in EPO-0 239 425. An HIV-1 virus is disclosed in WO 86/02383.

One characteristic of human immunodeficiency, viruses which complicates their comparison is their genetic variability,; genetic variants arise spontaneously and with high frequency. A comparison of various HIV-1 isolates revealed that some regions of the genome are highly variable while others are reasonably well conserved (5-10). Similar polymorphisms have also been observed for HIV-2 (11). The regions with the greatest genetic stability are presumably those regions coding for the regions of vital proteins which are structurally or enzymatically essential. The vital genes with the greatest overall genetic stability are the gag and pol genes, while some regions of the env gene and the genes coding for regulatory proteins such as rev. tat. sor and nef exhibit a high degree of variability. Some of the major structural features of the gag and pol gene products are apparently shared not only by all of the variants of a particular HIV-type, but have, at least to some extent, been conserved between virus types.

Antiserum produced against HIV-1 cross-reacts with the gag and pol gene products of HIV-2, albeit with a lower affinity than for the corresponding HIV-1 gene products, but no serological cross-reactivity is observed for the envelope proteins. However, in spite of the demonstrable immunological cross-reaction, there is only modest sequence homology at the nucleic acid level indicating that HIV-1 and HIV-2 are genetically distinct, and no significant hybridization between these two viruses can be detected except under very low stringency conditions (11).

The simian immunodeficiency viruses, or SIVs, are non-human primate lentiviruses that are the closest known relatives of the HIVs. SIVs have been previously isolated from macaques ($Siv_{mac}$) (12, 13), sooty mangabeys ($SIV_{sm}$) (14, 15), African Green Monkeys ($SIV_{AGM}$)(16) and mandrills ($SIV_{MND}$)(17).

Mangabeys, green monkeys and mandrills are African old world primates, whereas macaques are Asian old world primates. These four SIVs fall into three discrete groups based on genetic sequence analysis, with $SIV_{mac}$ and $SIV_{sm}$ forming a single genetic group (18). Macaques are apparently not infected with SIV in their native habitat (19). It seems likely, therefore, that some individual macaques became infected with $SIV_{sm}$ from sooty mangabeys at US Regional Primate Centers (20).

HIV-2 is no more different from $SIV_{sm}$ at the sequence level than individual $SIV_{sm}$ isolates are different from each other (18, 21).

$SIV_{AGM}$ and $SIV_{MND}$ are distinct from HIV-1 and HIV-2, $SIV_{MND}$ seems to be more or less equidistant from HIV-1 and HIV-2 (22) while $SIV_{AGM}$ is closer to HIV-2 than to HIV-1 (23). Serological cross-reactivity has been observed between structural proteins of different HIV/SIVs. At the level of the envelope proteins, cross-reactions exist between envelope proteins of $SIV_{mac}$, $SIV_{sm}$, $SIV_{AGM}$ and HIV-2, but sera from non-human primates infected with these viruses do not react to HIV-1 envelope proteins. Sera from $SIV_{MND}$ positive mandrills do not react with HIV-1 or HIV-2 envelope proteins.

In 1988, two cases of wild-born chimpanzees positive for HIV-1 antibodies were observed in the tropical rain forest of Gabon. A retrovirus was isolated from one of those chimpanzees and was designated as $SIV_{cpz-Gab-1}$. This virus was disclosed in French patent application nr. 89-02964, Mar. 7, 1989. The virus has been characterized by its growth characteristics, radio-immunoprecipitation and western blot to determine the molecular weight of the different proteins and the serological cross-reactivities (24). The virus has been sequenced and there is 84% homology with HIV-1 (25). This is the first retrovirus from non-human primates that belongs to the HIV-1 group of retroviruses.

In order to determine the spread and the importance of this infection, more chimpanzees were tested for HIV/SIV antibodies. A new case of a wild born chimpanzee positive for HIV-1 antibodies was observed. The isolation and characterization of a novel immunodeficiency virus from a chimpanzee of Zairian origin is described.

Geographically this virus comes from a region in Africa where HIV-1 is endemic. This isolate is shown immunologically to be antigenically more closely related to HIV-1 than to HIV-2.

Accordingly, the invention relates to a retrovirus isolated from a chimpanzee and designated as $SIV_{cpz-ant}$ and to variants of this virus, having the essential morphological and immunological properties of the retrovirus deposited in the European Collection of Animal Cell Cultures (ECACC) under accession number V 900 61 322.

A virus isolation was performed from blood from a young asymptomatic four year old male chimpanzee which had never received injections with infected material.

Serum from the chimpanzee was positive (ratio O.D./cut-off of 6) in the enzyme-linked immunosorbent assay (HIV 1+2 ELISA, Behring). On a commercial HIV-1 western blot (Dupont de Nemours), clear bands were observed at p24, p34, gp41, gp120 and gp160 and only weak bands at p55 and p68. Titers of the chimpanzee serum for the different HIV-1 antigens on a commercial western blot (Dupont de Nemours) are as follows:

p24:$\frac{1}{1000}$ p34:$\frac{1}{1000}$ gp41:$\frac{1}{50.000}$ gp120:$\frac{1}{10.000}$ gp160:$\frac{1}{100.000}$ The virus was isolated by co-cultivation of the chimpanzee's lymphocytes with PHA-stimulated lymphocytes from a healthy HIV-negative human donor, in a medium consisting of 1640 RPMI with 20 mM Hepes, and supplemented with 10% fetal calf serum, 2 μg/ml polybrene, antibiotics (100 μg/ml gentamicin) and 150 U/ml Interleukin-2. After 13 days in culture, the virus was detected in the culture on the basis of a positive HIV-1 antigen capture test (Innogenetics). The presence of reverse transcriptase (RT) was also detected in the culture supernalant (50.000 cpm). Cell free RT-and antigen positive-supernatant was used to passage the virus on fresh lymphocytes, and again a positive antigen capture test was observed and a reverse transcriptase activity was detected in the supernatant. No cytopathic effect with formation of giant cells was observed in lymphocytes. The virus was further propagated in PHA stimulated lymphocytes from healthy, human blood donors and was then transferred to continuous cell-lines of leukemic origin. Virus-containing supernatant was tested in parallel with culture supernatant known to contain HIV-1 in a differential antigen capturing test which is described in detail below. The results of this comparison indicated that the new isolate was close, although not identical, to HIV-1. The new virus was then characterized with respect to its protein antigens. The cell-lines used for propagating the virus can be lines of the CEM or MOLT-4 type, or an other immortalized cell-line which bears the T4 receptor on its cell-surface. Preferred cell-lines for the continuous propagation of $SIV_{cpz-ant}$ are MOLT-4 and CEM-SS cells. MOLT-4 cells infected with $SIV_{cpz-ant}$ were deposited with the ECACC on Jun. 13, 1990 under accession number V 900 61 322.

Establishment of a chronically infected cell line can, for example, be carried out as follows: MOLT-4 cells ($10^6$ cells/ml), preferably MOLT-4 clone 8 cells (obtained from N. Yamamoto, Yemaguchi, Japan), or CEM-SS cells (obtained from Peter Nara, Frederick, Md., U.S.A.), are cocultured with $SIV_{cpz-ant}$ infected-human lymphocytes ($10^6$ cells/ml) in RPMI 1640 culture medium buffered with 20 mM Hepes and containing 10% fetal calf serum. Virus production was followed using an antigen capture test (Innogenetics, Organon). With the CEM-SS cell line the antigen capture test became positive immediately and remained positive. With the MOLT-4 clone 8 cells, the antigen capture test became positive after 50 days of cocultivation. No cytopathic effect was observed in either cell line. Supernatants from these cells can be used as a source of virus.

Furthermore, the invention relates to a purified retrovirus having the essential morphological and immunological properties described below. In many cases, the unique characteristics of $SIV_{cpz-ant}$ can best be appreciated by comparison with the same type of characteristics relating to the other human immunodeficiency viruses HIV-1 and HIV-2, as well as the other simian immunodeficiency viruses, in particular the $SIV_{cpz-Gab}$ isolate from Gabon.

BRIEF DESCRIPTION OF THE DRAWINGS

1. Shows the reactivity of anti-$SIV_{cpz}$ sera on commercial HIV-1 western blot strips. The reactivities and titers of three different $SIV_{cpz}$ positive sera on HIV-1 western blot strips are shown:
   serum 1 serum form the animal from which $SIV_{cpz-Gab}$ was isolated.
   2 serum from the animal from which $SIV_{cpz-ant}$ was isolated.
   3 serum from the second chimpanzee from Gabon, from which no virus could be isolated.
2. Relates to the comparison of gag, pol and env proteins of HIV-1 (HTLV-IIIB), $SIV_{cpz-Gab}$ and $SIV_{cpz-ant}$ on western blot.

3. Relates to the comparison of proteins of HIV-1 (HTLV-IIIB), $SIV_{cpz-Gab}$ and $SIV_{cpz-ant}$ by radio-immunoprecipitation.
4. Relates to the comparison of proteins of HIV-1 (HTLV-IIIB), $SIV_{cpz-Gab}$, $SIV_{cpz-ant}$, HIV-2, $SIV_{AGM}$, $SIV_{MND}$, and $SIV_{MAC}$.
5. Shows antigen capturing of virus isolates using human polyclonal and mouse anti-HIV-1 monoclonal antibodies.
6. Comparison of the reactivity of $SIV_{cpz}$ antisera to different HIV/SIV types.
7. Electron microscopy.

MORPHOLOGY

Electron microscopy of $SIV_{cpz-ant}$ infected CEM-SS and MOLT-4 cells revealed the presence of budding and extracellular virus particles having a diameter of approximately 130 nm. $SIV_{cpz-ant}$ is morphologically very similar to the other known HIVs and SIVs, but it is readily distinguished from other human and simian retroviruses such as HTLV-I, HTLV-II and STLV-I.

PROTEIN AND GLYCOPROTEIN ANTIGENS

The virus present in the culture supernatant of $SIV_{cpz-ant}$ infected MOLT-4 cells was concentrated by overnight centrifugation at 19.000 rpm in a Beckman type 19Ti rotor. The resulting pellet was resuspended in electrophoresis sample buffer (62.5 mM Tris, pH 6.7, containing 2% 2-mercaptoethanol, 1% sodium dodecyl sulfate and 10% glycerol) and the principle viral antigens were separated by electrophoresis on a polyacrylamide gel (12.5% or 10%) under denaturing conditions. Molecular weight markers were included on the same gel so as to provide a basis for estimating molecular weights. Once separated, the proteins were electrophoretically transferred to nitrocellulose paper (Western blot) which was then incubated with an homologous antiserum. In this manner, the molecular weights of the $SIV_{cpz-ant}$ gag and pol and env gene products could be compared with those for HIV-1 and $SIV_{cpz-Gab}$. The apparent molecular weights observed for the $SIV_{cpz-ant}$ proteins are close to those observed for both HIV-1 and $SIV_{cpz-Gab}$. Nevertheless, small yet reproducible molecular weight differences between $SIV_{cpz-ant}$ and HIV-1 and $SIV_{cpz-Gab}$ proteins are also evident. The protein blots revealed that the major core protein $SIV_{cpz-ant}$ has a molecular weight of 27.000.

By convention, proteins are frequently referred to by a "p" for protein, or "gp" for glycoprotein, followed by a number which, when multiplied by 1.000, gives the approximate molecular weight of the polypeptide. The major core protein of $SIV_{cpz-ant}$ will be referred to hereafter as p27.

Figure 2:
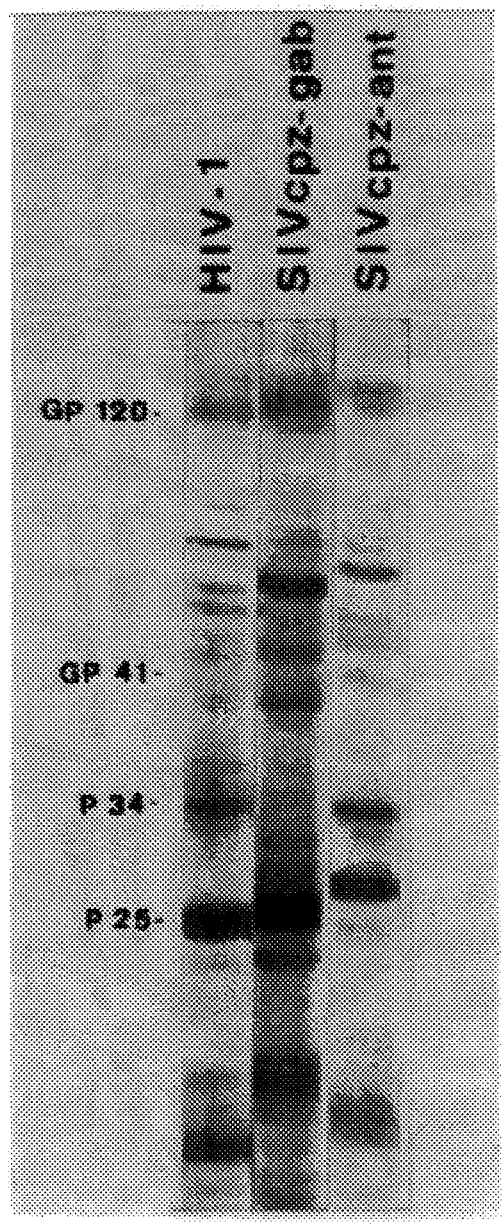

The molecular weight values as determined are expected to be correct to within 10% of the true values. Nevertheless, much confusion exists with regards to molecular weight values of proteins since the construction of the electrophoresis apparatus used and the source of the buffer components varies from laboratory to laboratory. It is therefore necessary when comparing the apparent molecular weights of the protein antigens of $SIV_{cpz-ant}$ with respect to those of HIV-1 or $SIV_{cpz-Gab}$ to subject all samples to electrophoresis on the same gel. Such a gel can, for example, be seen in FIG. 2. In particular, it is evident that while, in the case of the major core protein, the molecular weight values of the homologous proteins of the three viruses are very close, the protein derived from HIV-1 is the smallest. The major core protein of $SIV_{cpz-Gab}$ is somewhat larger then that of HIV-1, as has been previously reported (24). The homologous protein from $SIV_{cpz-ant}$ is larger than the major core protein of $SIV_{cpz-Gab}$. The calculated molecular weights of these proteins are given in Table 1.

TABLE 1

Comparison of molecular weights of gag and pol gene products.

| | gag | endonuclease | transmembrane protein | outer membrane |
| --- | --- | --- | --- | --- |
| HIV-1 | 25 | 34 | 41–45 | 120 |
| $SIV_{cpz-Gab}$ | 25.5 | 32 | 42–46 | 130 |
| $SIV_{cpz-ant}$ | 27 | 34 | 44–50 | 140 |

$SIV_{cpz-ant}$ possesses a pol gene-derived polypeptide which is an endonuclease with apparent molecular weight of 34.000 and which does not differ significantly in molecular weight from the homologous proteins from HIV-1.

When protein blots of the different viruses are each incubated with an homologous serum, obtained from an individual infected with this virus, the envelope proteins can be seen. These proteins are derived from the env gene and are the viral envelope glycoproteins. The smallest glycoprotein which is the transmembrane protein, migrates as a broad band with an apparent identical molecular weight for HIV-1 and $SIV_{cpz-Gab}$ of between 40.000 and 45.000, and with an apparently higher molecular weight for $SIV_{cpz-ant}$ of between 44.000 and 50.000.

The larger protein which is the outer membrane protein, has a molecular weight of 120.000 for HIV-1, has a somewhat higher molecular weight for the $SIV_{cpz-Gab}$ isolate and the highest molecular weight for the new isolate $SIV_{cpz-ant}$.

The glycoproteins are highly glycolysated and the apparent molecular weights which one observes is to same degree influenced by the cell line used to produce the virus. In order to determine differences between different viruses at the level of the envelope proteins, the viruses must be grown is the same cell-line.

In addition to the western blot, vital protein antigens can also be visualized by radio-immuno-precipitation assay (RIPA). For this purpose, viral proteins are metabolically labelled in vivo the virus infected cells in the presence of $^{35}S$-methionine (200 µCi per ml or $4.10^6$ cells/ml) in RPMI 1640 without methionine and supplemented with 10% fetal calf serum. After 16 hours the labeled virus is harvested from the supernatant and the cells in a lysis buffer (0.02M Tris pH7.6; 0.15M NaCl; 0.05M KCl; 0.001 mM EDTA; 0.2 mM PMSF; 0.05% aprotinin; 1% beta-mercaptoethanol and 2% Triton X-100).

Figure 3:
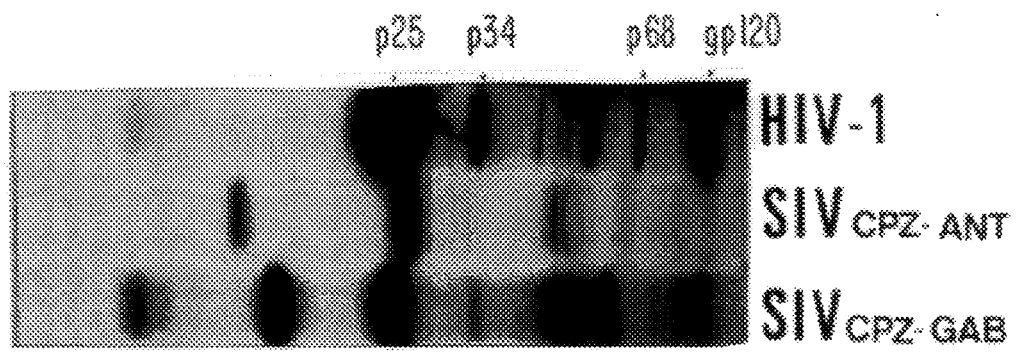

For immunoprecipitation, the equivalent of virus harvested in $2.10^6$ cells is reacted with 10 µl of a test serum in a buffer for 1 hour at 4° C. The resulting immune complexes are then bound on Protein-A-sepharose overnight at 4° C., washed extensively, and the bound proteins are eluted with electrophoresis sample buffer containing 1% SDS. The antigens are subsequently analyzed by electrophoresis, followed by fluorography and autoradiography. In FIG. 3, a RIPA is shown of HIV-1, $SIV_{cpz-Gab}$ and $SIV_{cpz-ant}$, in which each virus was precipitated with a homologous serum and analyzed on a 12.5% polyacrylamide gel. As with the western blot, we can see immediately the differences in molecular weight of the major core protein for the three viruses, with $SIV_{cpz-ant}$ having the highest molecular weight, as well as the differences for the external glycoproteins. The molecular weight of the external glycoprotein of $SIV_{cpz-ant}$ is higher than for $SIV_{cpz-Gab}$ or HIV-1. The three viruses were grown on the MOLT-4 cell-lines so that the differences in molecular weight are not due to cell line related factors.

Figure 4:
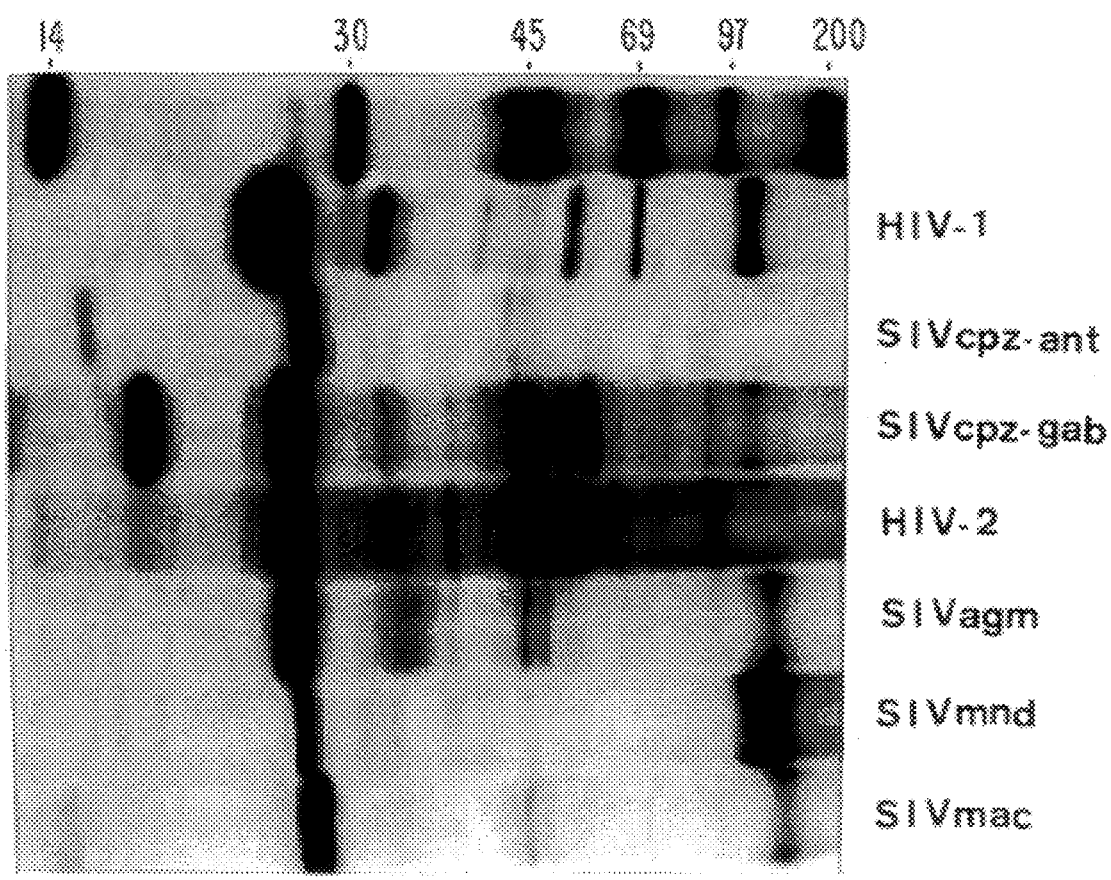
Figure 5:
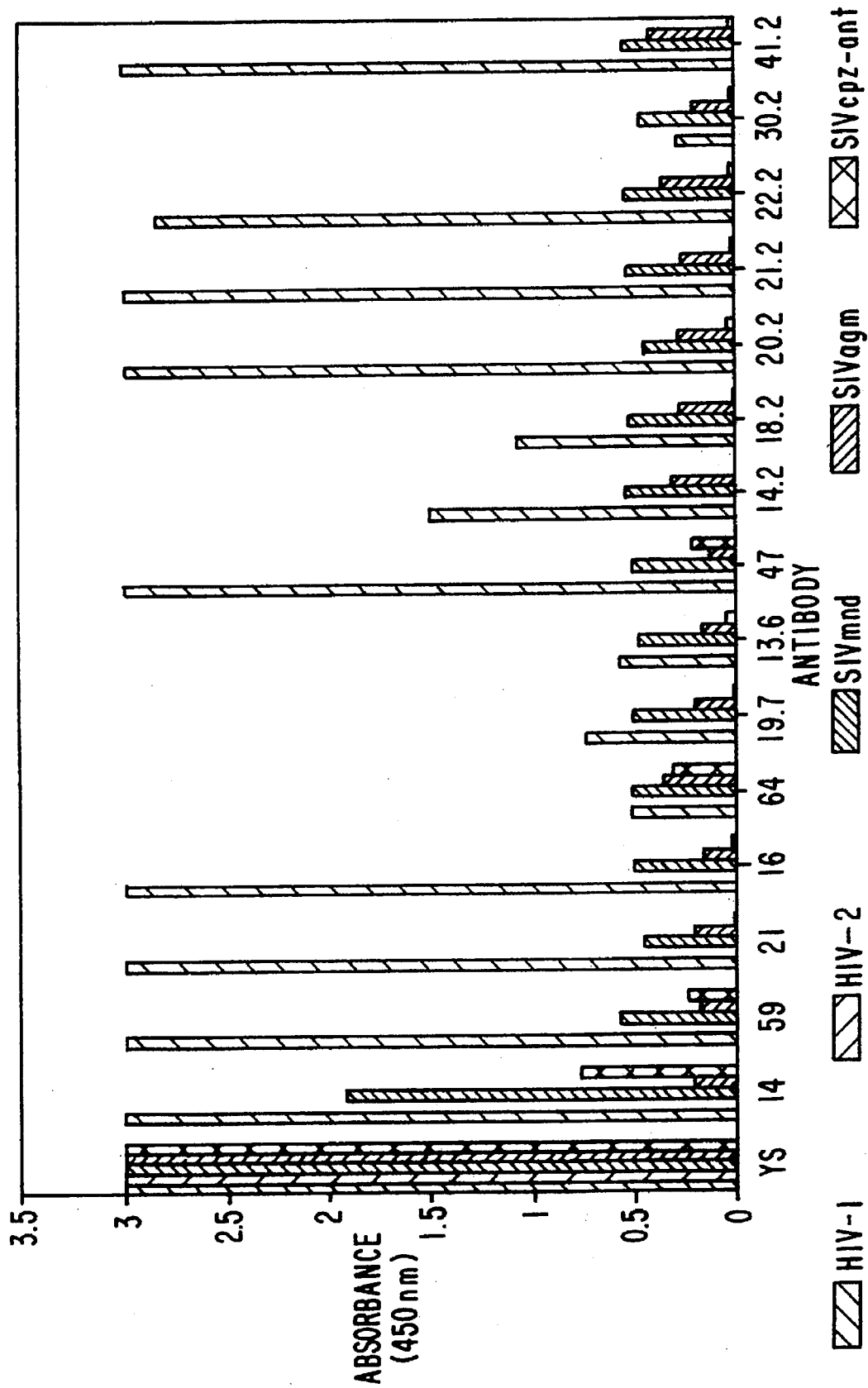

In FIG. 4 a RIPA on a 10% gel is shown of the different HIVs and SIVs, each precipitated with a homologous serum. The $SIV_{cpz-ant}$ isolate has a major core protein with a molecular mass that is higher than the other HIVs and SIVs shown.

The protein antigens of $SIV_{cpz-ant}$ can be characterized with respect to these of $SIV_{cpz-Gab}$, HIV-1 and other HIV/SIVs using two different but related approaches. On one hand, the antigens may be characterized on the basis of their ability to cross-react with antisera from individuals infected with HIV/SIV. On the other hand, antisera from chimpanzees infected with $SIV_{cpz-ant}$ and which contain antibodies produced in response to $SIV_{cpz-ant}$ antigens can be used to test cross-reactivity to the other HIV and SIV proteins. The antigenic relationships between $SIV_{cpz-ant}$ and the other HIV/SIVs are substantially illustrated in the examples given below. $SIV_{cpz-ant}$ is more closely related to HIV-1 and $SIV_{cpz-Gab}$, since an $SIV_{cpz-ant}$ antiserum cross-reacts with the gag, pol and env products of these viruses. $SIV_{cpz-ant}$ antiserum cross-reacts only with core proteins of HIV-2, $SIV_{mac}$, $SIV_{AGM}$, and $SIV_{MND}$ and never with the envelope proteins. Sera with antibodies to HW-2, $SIV_{mac}$, $SIV_{AGM}$, and $SIV_{MND}$ only cross-react with the core proteins of $SIV_{cpz-ant}$. Only anti-$SIV_{cpz}$ sera ($SIV_{cpz-ant}$ and $SIV_{cpz-Gab}$) react with gag, pol and env products of $SIV_{cpz-ant}$.

Of 25 HIV-1 positive sera tested, all the sera cross-reacted with gag and pol antigens, 5/25 reacted weakly with gp41, and only one of the 25 sera reacts with gp140 of $SIV_{cpz-ant}$. This serum is from a Cameroonian women from which an atypical HIV-1 virus was isolated.

In the examples which follow, it is demonstrated that $SIV_{cpz-ant}$ is substantially different from HIV-1 and the other chimpanzee isolate $SIV_{cpz-Gab}$ on the basis of 1. differences in molecular weight of source proteins
2. reaction with monoclonal antibodies
3. reaction of $SIV_{cpz-ant}$ antiserum with different HIV-1 proteins on western blot.

In addition, the invention relates to a composition comprising at least one antigen, in particular, a protein or glycoprotein of $SIV_{cpz-ant}$ retrovirus. Such a composition can be used in methods for detecting antibodies and in kits for carrying out such methods.

The $SIV_{cpz-ant}$ virus has proven to be a usable as a source of antigen for detecting antibodies in primates who have come into contact with $SIV_{cpz-ant}$ or an atypical HIV-1. As such, the virus may be grown and concentrated by the methods already described and a lysate prepared by treating the virus with a suitable detergent. A preferred detergent for preparing a total viral lysate is Triton X-100, used at a concentration of 0.5%. Another preferred detergent is Nonidet P40 (NP40), also used at a concentration of 0.5%.

Alternatively, vital protein may be purified from lysates of the virus. A preferred method for purifying these proteins is affinity chromatography. For example, the viral antigens may be separated on a preparative polyacrylamide gel and the individual antigens eluted in purified form. These may further be used to raise antisera in, for example, rabbits which are specific for the individual viral proteins.

The IgG fraction derived from immune rabbit serum can be coupled to a solid phase such as CNBr-activated Sepharose 4B (Pharmacia) and used to selectively remove individual viral antigens from viral lysates. These proteins may then be eluted from the affinity support using a low pH buffer and further purified using standard chromatographic techniques of which an example is given by Montelaro et al., J. of Virology (1982) 42: 1029–1030.

The invention relates generally to any composition which can be use for the diagnosis of $SIV_{cpz-ant}$ infection or for tests which have a prognostic value. These diagnostic procedures involve the detection of antibody in serum or other body fluid, which are directed against at least one of the antigens of $SIV_{cpz-ant}$.

Preferred compositions are viral lysates or purified antigens which contain at least one of the viral core proteins or envelope proteins or pol gene derived proteins. Especially preferred compositions are those which simultaneously contain, by way of example, the following proteins: p27 and gp140; p27 and gp44-50; p27, gp44-50 and gp140; and p27; p27, p34 and gp140. It should be understood however, that the above mentioned compositions are only meant to serve as examples and that the invention relates to all lysates or protein preparations containing one or more of the above mentioned proteins or glycoproteins.

The invention also relates to any composition in which either $SIV_{cpz-ant}$ viral lysate is used in combination with similarly prepared proteins derived from HIV-1 and/or HIV-2, and/or $SIV_{cpz-Gab}$, for the general diagnosis of infection or contact with immunodeficiency virus without regard to the absolute identity of the virus being detected. For example, such compositions could consist of a mixture of lysates of HIV-1, HIV-2, $SIV_{cpz-Gab}$, and $SIV_{cpz-ant}$ or could consist of the following:

- core proteins of HIV-1, HIV-2, $SIV_{cpz-Gab}$ and $SIV_{cpz-ant}$, and in particular, the major core protein of each virus type, homologous to the $SIV_{cpz-ant}$ p27 protein.
- envelope glycoproteins of HIV-1, HIV-2, $SIV_{cpz-Gab}$ and $SIV_{cpz-ant}$ and in particular the outer envelope glycoproteins of each virus type, homologous to $SIV_{cpz-ant}$ gp140.
- core proteins of HIV-1, HIV-2, $SIV_{cpz-Gab}$ and $SIV_{cpz-ant}$ together with the envelope glycoproteins of HIV-1, HIV-2, and $SIV_{cpz-ant}$ in particular the major core protein of each virus type, homologous to the $SIV_{cpz-ant}$ p27 protein, together with the major outer envelope protein of each virus, homologous to $SIV_{cpz-ant}$ gP 140.
- a combination of the core proteins and envelope proteins of HIV-1, HIV-2, $SIV_{cpz-Gab}$ and $SIV_{cpz-ant}$ and, in particular, homologous to the $SIV_{cpz-ant}$ proteins p27 and gp 140, respectively, and a protein derived from the pol gene of HIV-1, HIV-2, $SIV_{cpz-Gab}$ and $SIV_{cpz-ant}$, in particular the proteins of each virus type homologous to the p34 endonuclease protein of $SIV_{cpz-ant}$.

Furthermore, the invention relates to an antigen providing a single band in polyacrylamide gel electrophoresis, said antigen comprising, in common with one of the purified antigens of $SIV_{cpz-ant}$ retrovirus, an epitope that is recognized by serum of individuals carrying anti-$SIV_{cpz-ant}$ antibodies.

The amino acid sequences corresponding to these epitopes can readily be determined by isolating the individual proteins either by preparative electrophoresis or by affinity chromatography and determining the amino acid sequences of either the entire protein or the fragments produced enzymatically by trypsin or chymotrypsin digestion or by chemical means. The resulting peptide or polypeptides can subsequently be sequenced by Edman degradation. The invention relates therefore to any protein, glycoprotein or peptide, either derived directly from the virus or produced by cloning any cDNA fragments of the virus in bacterial expression vectors, or viral expression vectors for the expression of inserted DNA in mammalian or insect cells, and purifying the expressed protein by the methods described above. Furthermore, the invention also relates to synthetic peptides, produced either by Merrifield synthesis or Fmoc chemistry, which may be subsequently purified to homogeneity and which contain in their sequences epitopes which are shared by the natural $SIV_{cpz-ant}$, either by Western blotting, or radio-immunoprecipitation. In the case of small peptides which are not able to bind to nitrocellulose, these peptides can be detected by binding to nylon membranes (Pall Biodyne or Amersham) and reacting the membrane with anti-$SIV_{cpz-ant}$ antiserum. In particular, the invention relates to epitopes contained in any of the $SIV_{cpz-ant}$ core proteins, or in a protein which may contain a as part of its polypeptide chain epitopes derived from a combination of the core proteins. Furthermore, the invention relates to epitopes contained in either of the two $SIV_{cpz-ant}$ envelope glycoproteins, as well as any protein which contains, as part of its polypeptide chain, epitopes derived from a combination of the $SIV_{cpz-ant}$ envelope glycoprotein or a combination of the $SIV_{cpz-ant}$ core protein.

The invention additionally relates to polypeptides whose synthesis is directed by expression vectors constructed by recombinant DNA methods which incorporate epitopes derived from $SIV_{cpz-ant}$ proteins or glycoproteins together with epitopes derived from the proteins or glycoproteins of either HIV-1 and/or HIV-2 into a single polypeptide chain. Preparing such a construction would involve excising the relevant coding regions from cDNA of $SIV_{cpz-ant}$ as well as HIV-1 and HIV-2, and coupling the DNA in phase so as to form a coding sequence which, when inserted into an expression vector possessing the necessary signal sequences, directs the synthesis of a hybrid protein in which epitopes of the HIV-1, HIV-2, $SIV_{cpz-Gab}$ and $SIV_{cpz-ant}$ are contained.

Furthermore, the invention relates to methods for the detection of antibodies against SIV cpz-ant in a biological fluid, in particular for the diagnosis of a potential or existing ARC or AIDS caused by $SIV_{cpz-ant}$ retrovirus, characterized by contacting body fluid of a person to be diagnosed with a composition containing one or more of the proteins or glycoproteins of $SIV_{cpz-ant}$ or with a lysate of the virus, or with an antigen possessing epitopes common to $SIV_{cpz-ant}$ and detecting the immunological conjugate formed between the $SIV_{cpz-ant}$ antibodies and the antigen(s) used.

Preferred methods include, for example, immunofluorescence assays or immunoenzymatic assays. Immunofluorescence assays typically involve incubating, for example, serum from the person to be tested with cells infected with $SIV_{cpz-ant}$ and which have been fixed and permeabilized with cold acetone. Immune complexes formed are detected using either direct or indirect methods and involve the use of antibodies which specifically react to human immunoglobulins. Detection is achieved by using antibodies to which have been coupled fluorescent labels, such as fluorescein or rhodamine.

Immuno enzymatic assays may be performed, for example, as follows:

- a specific quantity of $SIV_{cpz-ant}$ virus extract or of a composition referred to according to the invention is deposited in the wells of a microtitration plate.
- the excess unbound material is removed after a suitable incubation period by washing.
- a suitable dilution or dilutions of serum of other body fluid which is to be tested for the presence of antibodies directed against one or more of the protein or glycoprotein antigen of $SIV_{cpz-ant}$ is introduced into the well.
- the microtitration plate is incubated for a period of time necessary for the binding reaction to occur.
- the plate is washed thoroughly.
- the presence of immune complexes is detected using antibodies which specifically bind to human immunoglobulins, and which have been labeled with an enzyme, preferably but not limited to either horseradish peroxidase, alkaline phosphatase, or beta-galactosidase, which is capable of converting a colorless or nearly colorless substrate into a highly colored product. Alternatively, the detection system may employ an enzyme which in the presence of the proper substrate(s), emits light.

the amount of product formed is detected either visually, spectrophotometrically, or luminometrically, and is compared to a similarly treated control.

Other detection systems which may also be used include those based on the use of protein A derived from *Staphylococcus aureus* Cowan strain I. protein G from group C Streptococcus sp. (strain 26RP66), or systems which employ the use of the biotin-avidin binding reaction.

Another method of immuno-enzymatic detection of the presence of antibodies directed against one or more of the $SIV_{cpz-ant}$ antigens is the Western blot. The viral antigens are separated electrophoretically and transferred to a nitrocellulose membrane or other suitable support. The body fluid to be tested is then brought into contact with the membrane and the presence of the immune complexes formed is detected by the method already described. In a variation on this method, purified viral antigen is applied in lines or spots and is subsequently brought into contact with the body fluid to be tested and the immune complexes formed are detected using the previously described techniques.

The presence of antibodies in body fluid may also be detected by agglutination. $SIV_{cpz-ant}$ lysates or a $SIV_{cpz-ant}$ lysate, antigen or purified antigen composition referred to according to this invention, is used to coat, for example, latex particles which form an uniform suspension. When mixed with serum containing antibodies to the antigen present, the latex particles are caused to agglutinate and the presence of large aggregates can be detected visually.

The present invention also relates to labeled extracts of $SIV_{cpz-ant}$ or compositions as previously described. The labeling can be of any type, such as enzymatic, chemical, fluorescent or radioactive.

Furthermore, the invention relates to a method for detecting the presence of $SIV_{cpz-ant}$ antigens in body fluids. This may, for example, be accomplished in the following manner:

the IgG fraction of antiserum, derived either from individuals infected with $SIV_{cpz-ant}$ or from animals injected with an $SIV_{cpz-ant}$ lysate or composition already described, is placed in the wells of a microtitration plate.

after a suitable period to allow adsorption, the excess unbound material is washed away.

a body fluid containing the antigen to be detected is placed in the well.

the microtitration plate is allowed to incubate for a suitable period of time to allow binding to occur.

the plate is then thoroughly washed with a suitable buffer.

the presence of bound antigen is detected either directly or indirectly, for example, by using immunoglobulins which are similarly specific for the antigen(s) to be detected and which have been labeled, preferably with one of the aforementioned enzymes.

an appropriate substrate is then added and the extent of reaction is compared to a control in order to measure the amount of antigen present.

Furthermore, the invention relates to a kit for the detection of anti-$SIV_{cpz-ant}$ antibodies in biological fluids, comprising an $SIV_{cpz-ant}$ lysate or a composition as referred to above and a means for detecting the immunological complexes formed.

In the case of kits designed to detect specific antibodies by immuno enzymatic methods such a kit would include:

an $SIV_{cpz-ant}$ lysate or composition of one of the types already described, preferably in a purified form, and preferably attached to a solid support such as a microtitration plate.

a conjugate between an enzyme and an immunoglobulin fraction which is capable of binding to the antibodies to be detected, or a conjugate between an enzyme and bacterial protein A or protein G.

a control antigen which possesses no epitopes which are shared by any human immunodeficiency virus.

appropriate buffers for performing the assay.

an appropriate substrate for the enzyme.

Kits for the detection of specific antibodies which make use of labeled antigen would include:

an appropriately labeled antigen or combination of antigens of the types already described.

Protein A or anti-human immunoglobulins, preferably coupled to an insoluble support, such as Protein A-sepharose 4B (Pharmacia) or an equivalent support.

control antiten, which is not recognized by anti-$SIV_{cpz-ant}$ antisera.

appropriate buffers for performing the assay.

if appropriate, substrates for the detection of enzymatically labeled antigen.

The invention further relates to kits, developed for the detection of $SIV_{cpz-ant}$ antigens in biological fluids, which comprise:

anti-$SIV_{cpz-ant}$ immunoglobulins, preferably coupled to a solid support such as a microtitration plate.

anti-$SIV_{cpz-ant}$ immunoglobulins conjugated to an enzyme.

negative control antigen, which would not be recognized by anti-$SIV_{cpz-ant}$ immunoglobulins.

positive control antigen which consists of one of the $SIV_{cpz-ant}$ antigens or compositions already described.

appropriate buffers for conducting the test. an appropriate substrate for detection of bound enzyme.

Furthermore, the invention relates to an immunogenic composition containing an envelope glycoprotein of $SIV_{cpz-ant}$ retrovirus, or a part of said glycoprotein, in combination with a pharmaceutically acceptable vehicle suitable for the constitution of vaccines effective against $SIV_{cpz-ant}$. The invention additionally relates to any peptide or polypeptide which contains within its sequence all or part of the protein backbone of the $SIV_{cpz-ant}$ retrovirus, as well as peptides which result from addition, substitution, or deletion of amino acids which do not affect the general immunological properties of said peptides.

The invention further relates to monoclonal antibodies characterized by their ability to specifically recognize epitopes contained in the $SIV_{cpz-ant}$ antigens or compositions as previously defined, and in particular, monoclonal antibodies raised specifically against said antigens and produced by traditional techniques. The invention also relates to monoclonal antibodies produced by immortalizing B-cells derived from primates infected with $SIV_{cpz-ant}$, for example, by transforming the B-cells with Epstein-Barr virus and subcloning the transformants.

The invention likewise relates to the production of polyclonal antisera in animals which recognize one or more $SIV_{cpz-ant}$ antigens and which is produced by infecting animals with purified $SIV_{cpz-ant}$ or an $SIV_{cpz-ant}$ antigen or combination of antigens, and in particular the proteins or glycoproteins of $SIV_{cpz-ant}$.

The antibodies, either polyclonal or monoclonal, can be used for a wide variety of purposes which include neutralization of $SIV_{cpz-ant}$ infectivity, the detection of $SIV_{cpz-ant}$ antigens in biological fluids or in infected cells, and the purification of $SIV_{cpz-ant}$ protein and glycoprotein antigens.

The invention further relates to nucleic acids, optionally labeled which are derived in part, at least, from RNA of $SIV_{cpz-ant}$ retrovirus or of variants of this virus.

The invention relates likewise to the use of cDNA or parts of the cDNA or the recombinants containing them, which are characterized by containing at least a portion of the cDNA corresponding to the entire genomic RNA of the $SIV_{cpz-ant}$ retrovirus. Such cDNAs may be used as probes for the specific detection of $SIV_{cpz-ant}$ sequences in biological fluids, tissues and cells. The probes are preferably also labeled, either radioactively or chemically, or alternatively, using enzymatic, fluorescent or chemiluminescent labels which enable the probes to be detected. Preferred probes for the specific detection of $SIV_{cpz-ant}$ and diagnosis of $SIV_{cpz-ant}$ infection are probes that contain all or a portion of the cDNA complementary to the $SIV_{cpz-ant}$ genome.

It is nevertheless understood that the probes which can be used for the diagnosis of $SIV_{cpz-ant}$ infection incorporate all sequences which originate from the $SIV_{cpz-ant}$ genome or its naturally occurring variants and includes sequences encoding the viral core proteins (gag gene), the two forms of reverse transcriptase, and the endonuclease (pol gene), as well as the two viral envelope glycoproteins (env gene).

The invention also relates to $SIV_{cpz-ant}$ nucleic acid sequences which have been incorporated into a recombinant nucleic acid comprising a nucleic acid from a vector, and having said cDNA or part of said cDNA inserted therein. Such a construction could be used for replicating the viral cDNA or its fragments in an organism or cell other than the natural host so as to provide sufficient quantities of the probe to be used for diagnostic purposes.

A probe generated in such a manner can be employed in a diagnostic test for specific detection of $SIV_{cpz-ant}$ which incorporates the following essential steps:

labeling of the probe generated as described above by the methods previously described.

bringing the probe into contact under stringent hybridization conditions with DNA from infected cells or viral RNA from infected cells or biological fluids, once said DNA or RNA has been, preferably, applied to a membrane and has been, preferably, applied to a membrane and has been rendered accessible to the probe.

washing the membrane with a buffer under circumstances in which stringent conditions are maintained.

detection of the labeled probe, preferably by autoradiography in cases in which the probe has been radioactively labeled, or by a suitable immunodetection technique in case the probe has been labeled chemically.

The invention further relates to a process for the production of $SIV_{cpz-ant}$ retrovirus characterized by culturing human T4 lymphocytes or human lymphocytic cell lines of leukemic origin which carry the T4 +phenotype with lymphocytes or cell lines that have previously been infected with an isolate of $SIV_{cpz-ant}$ retrovirus, as well as recovering and purifying the retrovirus from the culture medium. The invention likewise relates to a process for the production of antigens of $SIV_{cpz-ant}$ retrovirus, characterized by lysing the retrovirus, preferably with a detergent, and recovering the lysate containing said antigens.

The invention additionally relates to a process for the production of any of the $SIV_{cpz-ant}$ proteins or glycoproteins or reverse transcriptase as previously defined, or a part thereof, characterized by inserting the nucleic acid encoding the proteins or glycoproteins in an expression vector, transforming a host with said vector, culturing the transformed host as well as recovering and purifying the expressed protein.

The process includes vectors which may or may not direct the synthesis of fusion proteins and includes but is not limited to bacterial expression vector, mammalian expression vectors such as vaccinia virus, and vectors based on baculovirus for the expression of cloned genes in insect cells.

The invention relates also to the use of $SIV_{cpz-ant}$ for the development of a non-human primate model.

The development of such a model may for example, be accomplished in the following manner:

different non-human primate species should be infected with the virus.

the animals should be injected intravenously with the lymphocytes from an $SIV_{cpz-ant}$ infected chimpanzee or they should be injected intravenously with infected human cells showing a high liter of the $SIV_{cpz-ant}$ virus.

a persistent infection and its consequences should be examined by a clinical and biological follow-up of the infected animals at different time intervals. Various parameters which should be evaluated include the following:

clinical examination:
  general status
  lymphadenopathy
  reduced number of CD4$^+$ lymphocytes
  hepato- or splenomepathy
  fever, weight-loss
  development of symptoms of AIDS or AIDS-like diseases.

detection of antibodies, specific for $SIV_{cpz-ant}$ by western blot and RIPA using a specific $SIV_{cpz-ant}$ test.

virus-isolation from lymphocytes or plasma and measurement of antigenemia by a specific $SIV_{cpz-ant}$ test.

determination of the presence of neutralizing antibodies.

If persistent infection occurs, with or without development of AIDS, the infected primate can be used as a potential animal model for HIV-1, which can be utilized for testing vaccines and antiviral chemotherapeutic agents.

Vaccine evaluation may be accomplished by any number of well known techniques, all of which depend on the administration of immunogenic preparations containing one or more viral proteins in order to induce the production of antibodies or cytotoxic lymphocytes capable of conferring protection against a subsequent challenge with infectious virus. Preferred methods of vaccination include the administration of immunogenic compositions orally or by injection, the administration of killed or attenuated virus, the use of viral expression vectors such as vaccinia which express $SIV_{cpz-ant}$ proteins, and the oral administration of attenuated bacterial strains which express or secrete $SIV_{cpz-ant}$ proteins.

Antiviral chemotherapeutic agents may be evaluated by administering the agent according to an experimental protocol, the agent either prior to or after infection of the primate with $SIV_{cpz-ant}$. The efficacy of the agent in either preventing infection or inhibiting viral replication may be evaluated as outlined above.

The invention relates also to the use of non-human primates, persistently infected with $SIV_{cpz-ant}$ to evaluate new vaccines and antiviral products against HIV. In particular, antiviral chemotherapeutic agents may be evaluated in this system by comparing clinical symptoms before and after administration of the agent. In addition to the clinical symptoms, the evaluation would also include a determination of the levels of circulating viral antigen, the ease of virus isolation, a determination of immune function, and a quantitative estimation of virus load by employing appropriate primers and probes in the polymerase chain reaction (PCR).

EXAMPLES

Materials and methods

Virus and cell culture

A. Virus strains and cell lines

HIV-1 (HTLV-IIIB),HIV-2-rod(3),$SIV_{cpz-Gab-1}$ (24), $SIV_{MND-GB-1}$ (17), $SIV_{AGM-TYO-1}$ (16),$SIV_{MAC}$ (12), were used for purposes of comparison.

The cell-lines MOLT-4 clone 8 (provided by N. Yamamoto, Yamaguchi, Japan) and CEM-SS (Provided by P. Nara, Fredericksburg, Md., USA) were used for continuous virus production.

B. Virus isolations

Lymphocytes from the chimpanzees as well as from the healthy donors were isolated from heparinized whole blood on lymphoprep. (Nygaard and Co., Oslo, Norway). Lymphocytes from healthy donors were stimulated with 0.5 µg/ml phytohemagglutinin (PHA, Wellcome) in 1640 RPMI medium (GIBCO) containing 20 mM Hepes and supplemented with L-glutamine (0.03%/ml), 10% fetal calf serum, gentamycin (100 µg/ml). $5.10^6$ lymphocytes from the chimpanzee were cocultivated with $5.10^6$ PMA-stimulated donor lymphocytes at a final concentration of $1.10^6$ cells per ml in 1640 RPMI medium (GIBCO) containing 20 mM Hepes and supplemented with L-glutamine (0.03%/ml), 10% fetal calf serum (GIBCO), gentamycin (100 µg/ml) 2 µg/ml polybrene (Aldrich) and 150 U/ml Interleukin-2.

The medium was replaced with fresh medium every 3 to 4 days, at which time the cells were counted and the cell concentration was adjusted to $1.10^6$ cells/ml. Fresh PHA-stimulated lymphocytes were added to the isolation cultures when the cell concentration decreased. Every 3 to 4 days, cultures were also monitored for cytopathic effect and the presence of antigen in the culture supernatant by an antigen capturing test (Innogenetics, or Organon) and by reverse transcriptase activity.

In order to establish chronically infected, permanent cell-lines, virus infected primary lymphocyte cultures were co-cultivated with MOLT-4 clone 8 and CEM-SS cells. Virus production was monitored by the reverse transcriptase activity as well as antigen capturing.

Differential antigen capturing

A test system was developed whereby a distinction can be made between HIV-1 and other related human immunodeficiency viruses. The system is based on a comparison of the ability, of two different polyclonal IgG preparations, one with a broad anti-HIV specificity which is due to its exceptionally high titer, particularly against the major core protein, and one with a lower titer which reacts preferentially with HIV-1, to capture detergent-treated virus in culture supernatants. Detection of captured antigen is achieved by using a broad specificity IgG/horseradish peroxidase conjugate. The test detects primarily but not exclusively the p24 core protein.

Monoclonal Antibodies to HIV-1

8 of the 15 of monoclonal antibodies used have been described (26) and the remaining monoclonals used are made by Innogenetics. The antibodies were prepared against native viral proteins in Triton X-100 disrupted HIV-1 preparations.

Protein Analysis

A. Electrophoresis

Polyacrylamide gel electrophoresis of viral proteins was performed essentially as described by MAIZEL (27).

B. Protein blotting.

Blotting was performed either in a Bio-Rad transblot cell at 400 mA for 4 hours using the carbonate buffer described by Dunn (28).

Electron Microscopy $SIV_{cpz-ant}$ infected MOLT-4 and CEM-SS cells were fixed with glutaxaldehyde in cacodylate buffer, stained with osmium tetroxide and embedded in epon. Thin sections were stained with unancyl acetate and lead citrate and examined with a transmission electron microscope.

Radio Immunoprecipitation Assay

Infected cells were metabolically labelled with $^{35}$S-methionine overnight at 37° C. (200 µCi/ml at $4.10^6$ cells/ml). After collection of the supernatants and the cells, the virus was pelleted and then lysed in a lysis buffer (0.02M Tris pH 7.6; 0.15M NaCl, 0.05M KCl; 0.001 mM EDTA, 0.2 mM PMSF, 0.05% aprotinin; 1% beta-mercapto-ethanol and 2% Triton X-100). The diluted virus (the equivalent of virus harvested from $2.10^6$ cells) was then incubated with 10 µl serum for 1 h at 4° C. Immune complexes were adsorbed with protein A sepharose at 4° C. overnight. After washing, immune complexes were eluted in a sample buffer containing 1% SDS (sodium dodecyl sulphate) and beta-mercaptoethanol and heated at 100° C. for 3 min. They were then subjected to electrophoresis on a 12.5% or 10% SDS polyacry, lamide slab gel (SDS-PAGE). $^{35}$S-methionine labeled proteins were detected by fluorography and autoradiography.

Serology

Antibodies to HIV-1 and HIV-2 were assayed by commercial enzyme-linked immunosorbent assay (HIV-1+2 ELISA, Behring). The confirmatory tests used were commercial HIV-1 (Dupont de Nemours) and HIV-2 (Diagnostics Pasteur) Western blot.

Results

Serology

Figure 1:
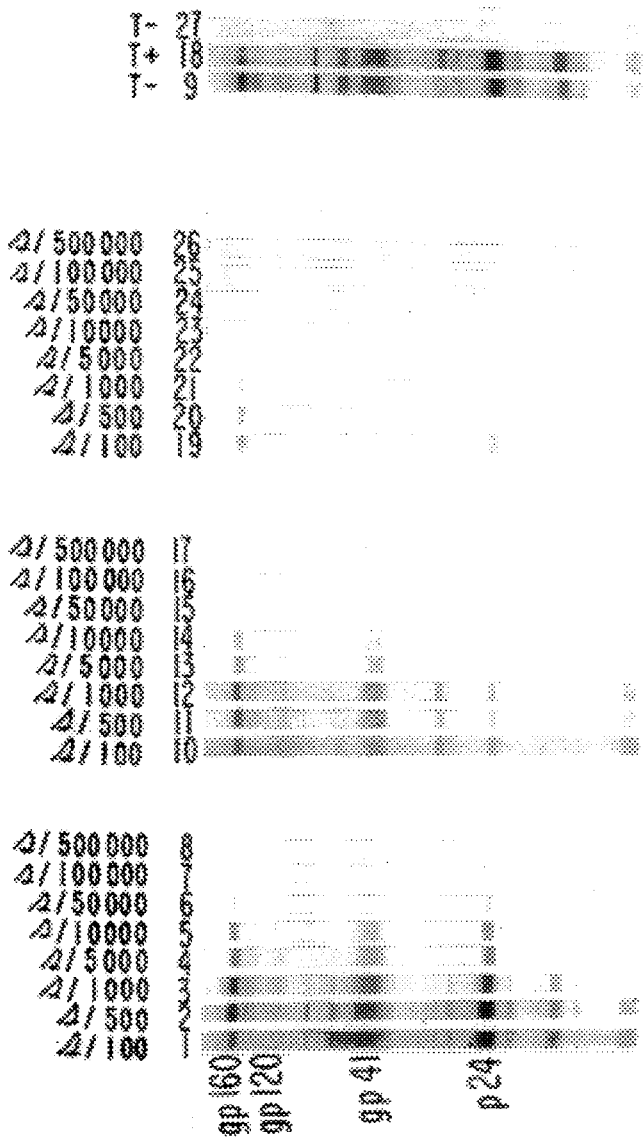

Serum from the chimpanzee was positive (ratio OD/cut-off=6) in the enzyme-linked immunosorbent assay. On a commercial HIV-1 western blot (Dupont de Nemours) clear bands were observed at p24, p34, gp41, gp120 and gp160, and only weak bands at p55 and p68. Titers of the chimpanzee serum for the different HIV-1 antigens on a commercial western blot (Dupont de Nemours) are shown in FIG. 1.

p24: 1/1000; p34:1/1000; gp41: 1/50,000; gp120: 1/10,000; gp 160: 1/100,000.

Virus Isolation

Virus was isolated by co-cultivation of the chimpanzees lymphocytes with PHA-stimulated lymphocytes from healthy uninfected human donors. After 13 days in culture, virus was detected in the culture as judged by a positive antigen capture test (Innogenetics, Organon). The presence of reverse transcriptase was also detected in the culture supernatant. No cytopathic effect with the formation of giant-cells was observed in lymphocytes. Cell-free culture supernatant was used to passage the virus on fresh lymphocytes. After seven days, a positive antigen capture test was observed and reverse transcriptase activity was detected in the supernatant. An attempt was made to transfer the virus to a permanent cell-line by co-cultivating the $SIV_{cpz-ant}$ infected primary lymphocytes with MOLT-4 clone 8 and CEM-SS cells.

Using the CEM-SS cell-line, reverse transcriptase activity was detected after seven days and the culture supernatant was positive in the antigen capture test. With the MOLT-4 clone 8 cells, the antigen capture test became positive only after fifty days of cocultivation. No typical cytopathic effect with the formation of giant cells was observed in these cell-lines.

Characterization of Viral Proteins

Virus in the culture supernatant was pelleted by an overnight centrifugation at 19.000 t/min. at 4° C. in a 19 Ti Beckman rotor. The pelleted virus was dissociated in SDS-sample buffer and analyzed by polyacrylamide gel electrophoresis followed by protein blotting. In FIG. 2, western blot strips of HIV-1 $SIV_{cpz-Gab}$ and $SIV_{cpz-ant}$ are shown.

Each virus lysate was reacted with a homologous serum, i.e. HIV-1 with an HIV-1 antibody-positive serum, $SIV_{cpz}$-GAB virus with the serum from the animal from whom the virus was isolated, and $SIV_{cpz-ant}$ virus was reacted with the serum from the chimpanzee from which the virus was isolated.

From the figure it is evident that the molecular weights of the $SIV_{cpz-ant}$ gene products differ from those of HIV-1 and $SIV_{cpz-Gab}$. A comparison of the molecular sizes of the proteins are shown in table 1.

The most important differences are the molecular weights of the major core protein (p27 versus P25 for HIV-1 and p25.5 for $SIV_{cpz-Gab}$) and the molecular weight of the external glycoproteins. The cell-line used for propergating the viruses (HIV-1, $SIV_{cpz-Gab}$ and $SIV_{cpz-ant}$) was the MOLT4 clone 8 cell-line, this makes that the differences observed between the three viruses are not influenced by different cell-lines.

In addition to the western blot, viral protein antigens can also be visualized by radio immunoprecipitation (RIPA). For this purpose, MOLT-4 clone 8 cells were infected with the viruses and the viral proteins were metabolically labeled with $^{35}$S-methionine. Labeled virus is harvested from the supernatants and the cells. In FIG. 3 is shown a RIPA of HIV-1, $SIV_{cpz-Gab}$ and $SIV_{cpz-ant}$. The labeled viruses were harvested from the culture supernatants and each virus was precipitated with an homologous serum. As observed on western blots, one can see that the molecular weights of the $SIV_{cpz-ant}$ gene products differ from these of HIV-1 and $SIV_{cpz-Gab}$. The major core protein and the external glycoprotein of $SIV_{cpz-ant}$ have higher molecular weights than the corresponding proteins of HIV-1 and $SIV_{cpz-Gab}$.

In FIG. 4, a RIPA of different HIV and SIVs is shown, each precipitated with a homologous serum in order to better determine the differences between the viruses. i.e. HIV-1 virus+HIV-1 antibody positive serum, $SIV_{cpz-Gab}$ with the serum from the animal from whom the virus was isolated, $SIV_{cpz-ant}$ virus with the serum from the animal from which the virus was isolated, HIV-2 with an HIV-2 antibody-positive serum, $SIV_{AGM-TYO}$ with an $SIV_{agm}$ antibody-positive serum, $SIV_{MND}$ with a $SIV_{MND}$ antibody-positive serum, and $SIV_{mac}$ with an $SIV_{mac}$ antibody-positive serum. The figure again shows the differences in molecular weight.

Cross Reactivity of Mouse Monoclonal Antibodies Directed Against HIV-1 P24 Core Protein A panel of mouse monoclonal antibodies (MAbs) prepared against the HIV-1 p24 core protein was tested for their ability to cross-react with HIV-1, HIV-2, $SIV_{mnd}$, $SIV_{AGM}$ and $SIV_{cpz-ant}$ isolates. In principle, any panel of anti-HIV-1 p24 monoclonal antibodies can be used, as long as the series includes monoclonal antibodies which react with different epitopes on the HIV-1 p24 molecule. Ascites fluid containing the antibodies was diluted and used to coat microwell plates. Detergent-treated, virus-containing supernatants were then added to the coated wells. Bound antigen was detected using broad specificity anti-HIV IgGs conjugated to horseradish peroxidase. The results obtained are shown in FIG. 5.

In control wells coated with polyclonal broad spectrum IgGs, all virus-containing supernalants gave optical densities which exceeded the limits of the microwell plate reader. However, when tested in wells coated with the various monoclonal antibodies, quite a different pattern emerged. Previous studies indicated that the MAbs tested react against at least seven epitopes on the p24 molecule.

The $SIV_{cpz-ant}$ isolate has the weakest reaction with the different monoclonals that even tested. This results indicate that the $SIV_{cpz-ant}$ differs from the other HIV/SIVs tested at the level of the p24 antigen.

Serological Cross-Reactions

The antigenic relationship between $SIV_{cpz-ant}$ and the other HIV/SIVs are substantially illustrated in the examples given below. $SIV_{cpz-ant}$ is more closely related to HIV-1 and $SIV_{cpz-Gab}$, since a $SIV_{cpz-ant}$ antiserum cross-reacts with the gag, pol and env products of these viruses, and only will the core proteins of the other viruses (HIV-2, $SIV_{mac}$, $SIV_{AGM}$, and $SIV_{mnd}$). Sera with antibodies to HIV-2, $SIV_{mac}$, $SIV_{AGM}$, and $SIV_{mnd}$ only cross-react with the core proteins of $SIV_{cpz-ant}$.

Only anti-$SIV_{cpz}$ sera ($SIV_{cpz-ant}$ and $SIV_{cpz-Gab}$) react with gag, pol and env products of $SIV_{cpz-ant}$. Among 25 HIV-1 positive sera, all of the sera cross-react with gag and pol antigens, 5 react weakly with gp41, and only one serum reacts with the gp 120 band of $SIV_{cpz-ant}$. The serum that reacts with the gp120 band is from a Cameroonian woman from which an atypical HIV-1 virus was isolated.

Discussion

A novel immunodeficiency virus has been isolated from a wild-born chimpanzee. The animal has never been experimentally infected and has never received human blood products. The animal is in good health, and shows actually no signs of AIDS or AIDS-like diseases.

The virus seems to be close to HIV-1 on the basis of the serological cross-reaction of the $SIV_{cpz-ant}$ positive serum with HIV-1 antigens on western blot.

However, there are several arguments that indicate, that the virus is different from HIV-1.

the differing molecular weights of the viral proteins.

a different pattern of cross-reactivity with anti-HIV-1 antiserum than HIV-1 a drastically reduced ability to be recognized by mouse monoclonal antibodies raised against p24 core proteins.

The $SIV_{cpz-ant}$ virus is also different from the other chimpanzee isolate from Gabon ($SIV_{cpz-Gab}$) on the basis of the differing molecular weights of the viral protein.

FIG. 1

Reactivity of 3 positive chimpanzee sera for the different HIV-1 antigens on a commercial western blot (Dupont de Nemours).

Serum 1: serum from the animal from which $SIV_{cpz-Gab}$ was isolated.

Serum 2: serum from the animal from which $SIV_{cpz-ant}$ was isolated.

Serum 3: serum from the second chimpanzee from Gabon, from which no virus could be isolated.

FIG. 2

Comparison of gag, pol and env proteins of HIV-1 (HTLV-IIIB), $SIV_{cpz-Gab}$ and $SIV_{cpz-ant}$ by Western blot.

The viral lysates were separated on the same polyacrylamide gel (10%). Each virus was reacted with a homologous serum.

lane 1: HIV-1 (HTLV-IIIB) with an HIV-1 positive serum.

lane 2: $SIV_{cpz-Gab}$ with the serum from the animal from which the virus was isolated.

lane 3: $SIV_{cpz-ant}$ with the serum from the animal from which the virus was isolated.

FIG. 3

Comparison of gag, pol and env proteins of HIV-1 (HTLV-IIIB), $SIV_{cpz-Gab}$ and $SIV_{cpz-ant}$ by Radio-Immuno-Precipitation (RIPA).

The viral proteins were separated on a 12.5% polyacrylamide gel. Each virus was precipitated with a homologous serum.

lane 1: HIV-1 (HTLV-IIIB) with an HIV-1 antibody positive serum.

lane 2: $SIV_{cpz-ant}$ with the serum from the animal from which the virus was isolated.

lane 3: $SIV_{cpz-Gab}$ with the serum from the animal from which the virus was isolated.

FIG. 4

Comparison of proteins of different HIVs and SIVs by RIPA.

The viral proteins were separated on 10% polyacrylamide gel. Each virus was reacted with a homologous serum lane 1: HIV-1 (HTLV-IIIB) with an HIV-1 antibody positive serum.

lane 2: $SIV_{cpz-ant}$ with the serum from the animal from which the virus was isolated.

lane 3: $SIV_{cpz-gab}$ with the serum from the animal from which the virus was isolated.

lane 4: HIV-2-rod with an HIV-2 antibody positive serum.

lane 5: $SIV_{AGM-TYO}$ with an $SIV_{AGM}$ antibody positive serum.

lane 6: $SIV_{MND-GB-1}$ with an $SIV_{MND}$ antibody positive serum.

lane 7: $SIV_{MAC}$, with an $SIV_{MAC}$, antibody positive serum.

FIG. 5

Antigen capturing of different virus isolates using human polyclonal and mouse anti-HIV-1 p24 monoclonal antibodies.

HIV-1 (HTLV-IIIB)
HIV-2 rod
$SIV_{MND-GB-1}$
$SIV_{AGM-TYO}$
$SIV_{cpz-ant}$

FIG. 6a

HIV-2 ROD labeled with $^{35}$S-methionine was precipitated with different sera.

lane 1: $SIV_{cpz-ant}$ antibody-positive serum.

lane 2: $SIV_{cpz-Gab}$ antibody-positive serum.

lane 3: serum from the second positive chimpanzee from Gabon, from which no virus isolate was obtained.

lane 4: HIV-1 antibody-positive serum.

lane 5: HIV-2 antibody-positive serum.

FIG. 6b $SIV_{mnd-Gab-1}$ labeled with $^{35}$S-methionine was precipitated with different sera.

lane 1: $SIV_{cpz-ant}$ antibody-positive serum.

lane 2: $SIV_{cpz-aGab}$ antibody-positive serum.

lane 3: Serum from the second positive chimpanzee from Gabon, from which no virus isolate was obtained.

lane 4: HIV-1 antibody-positive serum.

lane 5: HIV-2 antibody-positive serum.

lane 6: $SIV_{AGM}$ antibody-positive serum.

lane 7: $SIV_{mnd}$ antibody-positive serum.

Figure 6C:
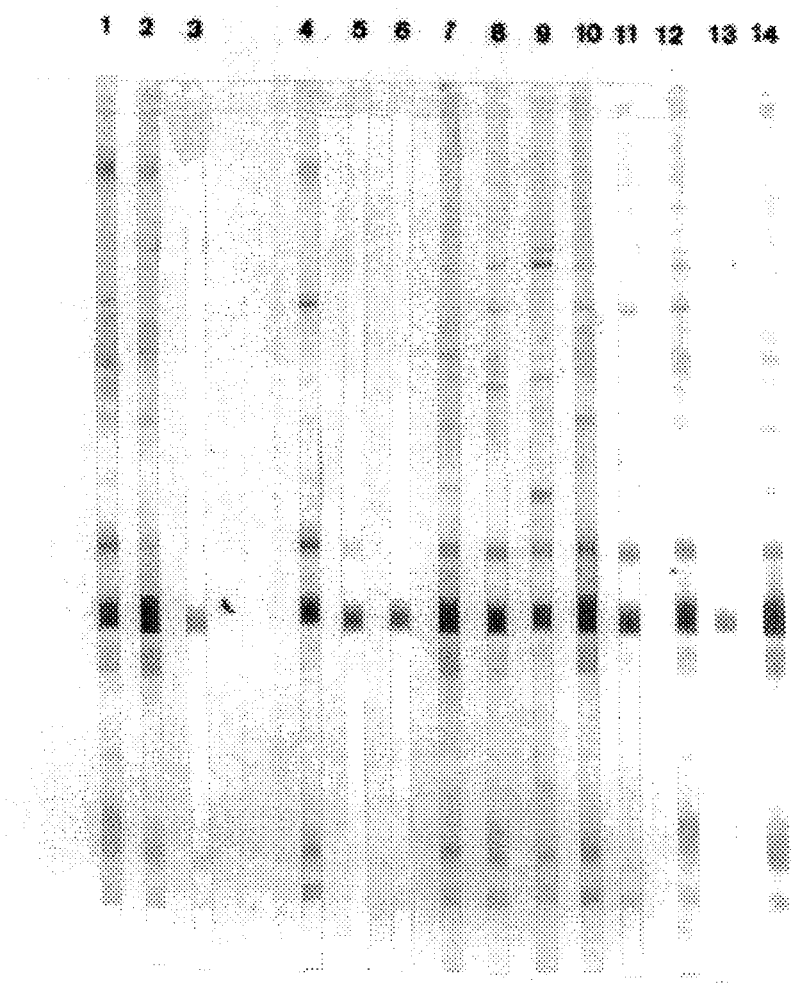
Figure 7:
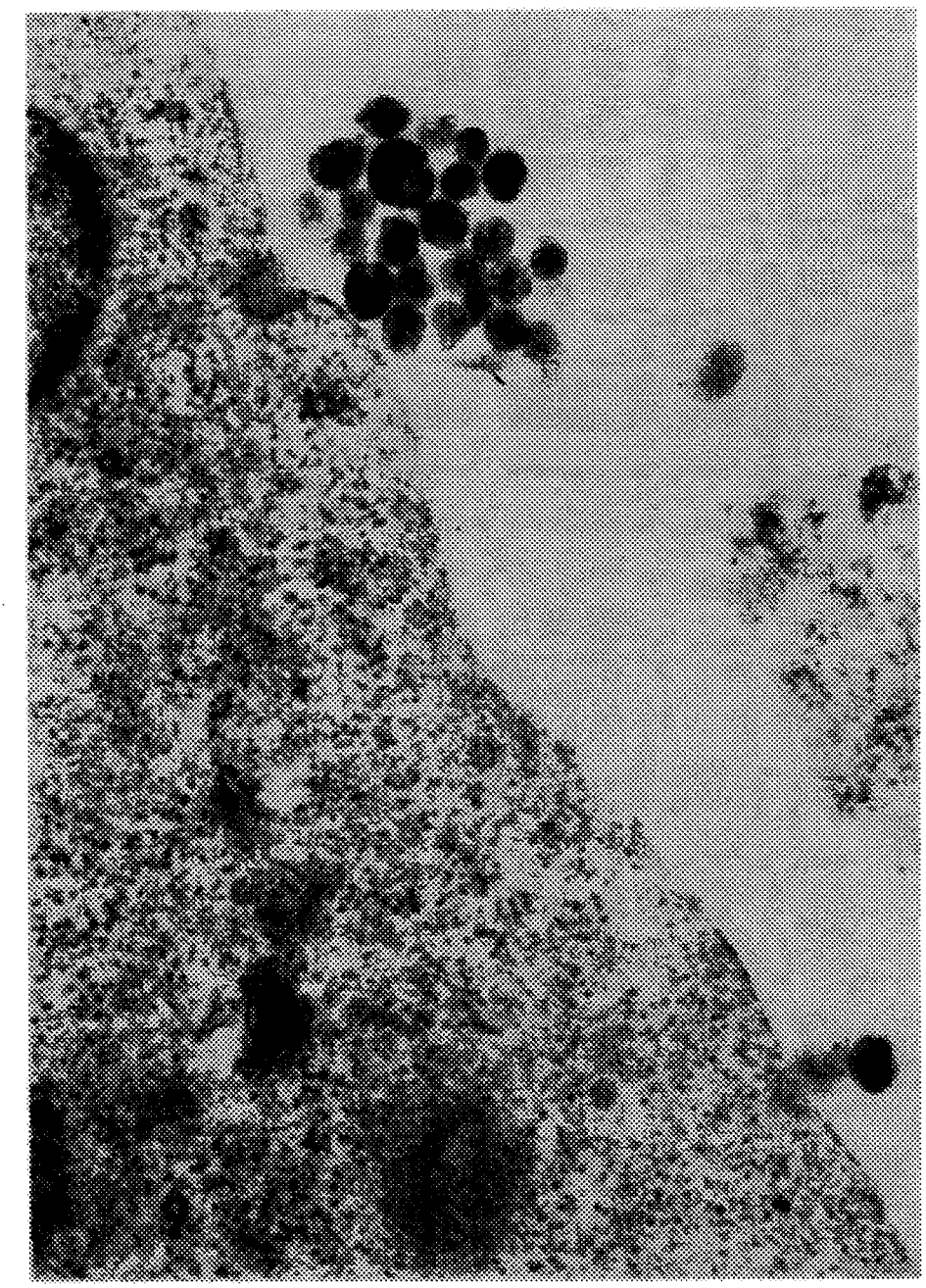

FIG. 6c western blot strips with $SIV_{cpz-ant}$ antigen were incubated with different sera.

lane 1: $SIV_{cpz-ant}$ antibody-positive serum.

lane 2: $SIV_{cpz-aGab}$ antibody-positive serum.

lane 3: Serum from the second positive chimpanzee from Gabon, from which no virus isolate was obtained.

lane 4: serum from a Cameroonian woman from which an atypical HIV-1 ($HIV-1_{ant70}$) was isolated.

lane 5 to 14: HIV-1 antibody-positive sera.

FIG. 7

Electron microscopic demonstration (×27.000) of the presence of $SIV_{cpz-ant}$ virions.

References

1. Dalgleish, A. G., Beverly, P. C. L., Clapham, P. R., Crawford, D. H., Greaves, M. F. and Weiss, R. A. (1984).

The CD4 (T4) antigen is an essential component of the receptor for the AIDS retrovirus.

*Nature* 312:763–766.

2. Maddon, P. J., Dalgleish, A. G., McDougal, J. S., Clapham, P. R., Weiss, T. A. and Axel, R. (1986).

The T4 gene encodes the AIDS virus receptor and is expressed in the immune system and the brain.

*Cell* 47:333–348.

3. Clavel, F., Guetard, D., Brun-Vezinet, F., Chamaret, S., Rey, M. A., Santos-Ferreira, M. D., Laurent, A. G., Dauguet, C., Katlama, C., Rouzioux, C., Klatzmann, D., Champalimaud, J. L. and Montagnier, L. (1986).

Isolation of a new human retrovirus from West-African patients with AIDS.

*Science* 233:343–346.

4. Albert, J., Bredberg, U., Chiddi, F., Bottinger, B., Fenyo, E. M., Norrby, E. and Biberfeld, G. (1987).

New pathogenic human retrovirus of West-African origin (SBL 6669) and its relationship to HTLV-IV, LAV-II and HTLV-IIIB.

*AIDS Res*

5. Benn, S., Ruthledge, R., Folks, T., Gold, J., Baker, L., McCormick, J., Feorino P;, Piot, P., Quinn, T., and Martin, M. (1985).

Genomic heterogeneity of AIDS retroviral isolates from North America and Zaire.

*Science* 230:949–951.

6. Hahn, B. H., Show, G. M., Taylor, M. E., Redfield, R. R., Markham, P. D., Salahuddin, S. Z., Wong-Staal, F., Gallo, R. C., Parks, E. S. and Parks, W. P. (1986).

Genetic variation in HTLV-III/LAV over time in patients with AIDS or at risk for AIDS.

*Science* 232:1548–1553.

7. Magasiny, S., Spire, B., Barré-Sinoussi, F. and Chermann, J. -C. (1986).

Genomic variability of selected LAV-related AIDS retroviruses.

*AIDS Res.* 2:19–30.

8. Alizon, M., Wain-Hobson, S., Montagnier, L. and Sonigo, P. (1985).

Genetic variability of the AIDS virus: nucleotide sequence analysis of two isolates from African patients.

*Cell* 46:63–74.

9. Starcich, B. R., Hahn, B. H., Shaw, G. M., McNeely, P. D., Modrow, S., Wolf, H., Parks, E. S., Parks, W. P., Josephs, S. F., Gallo, R. C., Wong-Staal, F. (1986).

Identification and characterization of conserved and variable regions in the envelope gene of HTLV-III/LAV, the retrovirus of AIDS.

*Cell* 45:637–648.

10. Willey, R. L., Ruthledge, R. A., Dias, S., Folks, T., Theodore, T., Buckler, C. E. and Martin, M. A. (1986).

Identification of conserved and divergent domains within the envelope gene of the exquired immunodeficiency syndrome retrovirus.

*Proc. Natl. Acad, Sci. USA:* 83:5038–5042.

11. Clavel, F., Guyader, M., Guetard, D., Sallé, M., Montagnier, L., and Alizon, M. (1986).

Molecular cloning and polymorphism of the human immune deficiency virus type 2.

*Nature:* 324:691–695.

12. Daniel, M. D., Letvin, N. L., King, N. W. et al. (1985).

Isolation of T-cell tropic HTLV-III-like retrovirus from macaques.

*Science:* 228:1201.

13. Benvenista, R. E., Arthur, L. O., Tsai, C. C., et al. (1986).

Isolation of a lentivirus from a macaque with lymphoma. Comparison with HTLV-III/LAV and other lentiviruses.

*J. Virol.* 60:483490.

14. Fultz, P. N., McClure H. M., Anderson, D. C., Swenson, R. B., Anand, R., Srinivasan, A. (1986).

Isolation of a T-lymphotropic retrovirus from naturally infected sooty mangabey monkeys (Cercocebus atys).

*Proc. Natl. Acad. Sci. USA* 83:5386–5290.

15. Lowenstine, L. J., Pedersen, M. C., Higgins et at. (1986).

Sero-epidemiologic survey of captive old-world primates for antibodies to human and simian retroviruses, and isolation of a lentivirus-from sooty mangabeys (Cercocebus atys).

*Int. J. Cancer* 38:563–574.

16. Otha, Y., Msauda, T., Tsujimoto, H., et al. (1988).

Isolation of simian immunodeficiency virus from African green monkeys and sero-epidemiologic survey.

*Int. J. Cancer* 41:115–122.

17. Tsujimoto, H., Cooper, R. W., Kodama, T., et al. (1988).

Isolation and characterization of simian immunodeficiency virus from mandrills in Africa and its relationship to other human and simian immunodeficiency viruses.

*J. Virol.* 62:4044–4050.

18. Hirsch, V., Olmsted. R., Murphey-Cars, M., Purcell, R., Johnson, P., (1989).

An african primate lentivirus $SIV_{sm}$ closely related to HIV-2.

*Nature* 339:389–392.

19. Daniel, M., Letcin, N., Seghal, P., Schmidt, D., Silva, D., Solomon, K., Hodi, F., Ringler, D., Hunt, R., King, N., Desrosiers, R. (1988).

Prevalence of antibodies to 3 retroviruses in a captive colony of macaque monkeys.

*Int. J. Cancer* 41:601–608.

20. Murphey-Cars, M., Martin, L, Rangam S., Baskin, G., Gormus, B., Wolf, R., Andes, W., West, M., Montelenaro, R. (1986).

Isolation of an HTLV-III related retrovirus from macaques with simian AIDS and its possible origin in asymptomatic mangabeys.

*Nature* 321:435–437.

21. Desrosiers, R., Daniel, M., Li, Y. (1989).

Minireview, HIV-related lentiviruses of non-human Primates.

*AIDS Research and human retroviruses* 5: 465–473.

22. Tsujimoto, N., Hasegawa, A., Maki, N., Fukasawa, M;, Miura, T., Speidel, S., Cooper, R., Moriyama, M., Gojobori, T., Hayami, M. (1989).

Sequence of a novel simian immunodeficiency virus from a wild-caught mandrill.

*Nature* 341:539–541.

23. Fukasawa, M., Miura, T., Hasegawa, A., et al. (1988).

Sequence of simian immunodeficiency virus from African green monkey, a new member of the HIV/SIV group.

*Nature* 333:457–461.

24. Peeters, M., Honore, C., Huet, T., Bedjadaga, L., Ossari, S., Bussi, Ph., Cooper, R., Delaporte, E. (1989).

Isolation and partial characterization of an HIV-related virus occurring naturally in chimpanzees in Gabon.

*AIDS* 3:625–630.

25. Huet. T., Cheynier, R., Meyerhans, A., Roelants, G., Wain-Hobson, S. (1990).

Genetic organization of a chimpanzee lentivirus related to HIV-1.
*Nature* 345:356–358.

26. Winkel, I. N., Tersmette, M., Miedema, F. and Huisman, J. G. (1987).
Identification of gag-epitopes by a panel of MAb in a series of HIV isolates.
*Abstracts of the Third International Conference on AIDS, Washington D.C., USA* p. 116.

27. Maizel, J. V. (1971).
Polyacrylamide gel electrophoresis of viral proteins; in *Methods in Virology*, Vol. 5, pp: 180–246, K. Maramorusch and H. Koprowski, Editor, Academic Press, New York, London.

28. Dunn, S. D. (1986).
Effects of the modification of transfer buffer composition and the renaturation of proteins in gels on the recognition of proteins on Western blots by monoclonal antibodies.
*Anal. Biochem,* 157:144–153.

We claim:

1. An isolated and purified simian immunodeficiency virus designated $SIV_{cpz-ant}$ having the essential biochemic, morphologic, and immunologic properties of the $SIV_{cpz-ant}$ deposited at the European Collection of Animal Cell Cultures (ECACC) under biological deposit no. V 900 61 322, wherein said essential properties comprise the following:

a. the virus exhibits a tropism for T4 lymphocytes;
   b. the virus is noncytopathic in tissue culture;
   c. the virus does not induce syncytia formation in tissue culture;
   d. the virus has a diameter of approximately 130 nm;
   e. the virus possesses a $Mg^{2+}$-dependent reverse transcriptase activity;
   f. the virus can be propagated in T4 immortalized cell lines;
   g. viral lysates contain a viral protein, designated p27, with an apparent molecular weight of 27 kDa as determined by SDS-PAGE;
   h. viral lysates contain a viral protein, designated p34, with an apparent molecular weight of 34 kDa as determined by SDS-PAGE;
   i. viral lysates contain a viral glycoprotein, designated gp44-50, with an apparent molecular weight of 44–50 kDa as determined by SDS-PAGE; and,
   j. viral lysates contain a viral glycoprotein, designated gp140, with an apparent molecular weight of 140 kDa as determined by SDS-PAGE.

2. A viral lysate containing antigens of $SIV_{cpz-ant}$ of claim 1.

3. An isolated and purified viral antigen obtained from the $SIV_{cpz-ant}$ of claim 1, designated p27, wherein said p27 antigen has an apparent molecular weight of 27 kDa as determined by SDS-PAGE.

4. An isolated and purified viral antigen obtained from the $SIV_{cpz-ant}$ of claim 1, designated p34, wherein said p34 antigen has an apparent molecular weight of 34 kDa as determined by SDS-PAGE.

5. An isolated and purified viral antigen obtained from the $SIV_{cpz-ant}$ of claim 1, designated gp44-50, wherein said gp44-50 antigen has an apparent molecular weight of between 44 and 50 kDa as determined by SDS-PAGE.

6. An isolated and purified viral antigen obtained from the $SIV_{cpz-ant}$ of claim 1, designated gp140, wherein said gp140 antigen has an apparent molecular weight of 140 kDa as determined by SDS-PAGE.

7. An immunogenic composition comprising an antigen obtained from the $SIV_{cpz-ant}$ of claim 1, wherein said antigen is selected from the group consisting of p27, p34, gp44-50 and gp140.

8. A method for the detection of primate antibodies in a biological sample that display immunological cross-reactivity towards $SIV_{cpz-ant}$ viral antigens comprising the following:

a. obtaining and preparing a biological sample from a primate;
   b. attaching the viral lysate of claim 2, or one or more of the viral antigens of claims 3, 4, 5, or 6, to a solid support;
   c. incubating said biological sample with the viral lysate or viral antigens of step (b) under conditions that promote antigen-antibody binding and the formation of antigen-antibody immune complexes on the solid support;
   d. washing the solid support of step (c) containing said antigen-antibody complexes to remove any residual unbound antibodies in the biological sample;
   e. detecting the presence of said immune complexes formed in step (c) by incubating the solid phase with a labeled primate-specific antibody under conditions that promote labeled antibody binding to the immune complexes;
   f. washing the solid support to remove unbound labeled primate-specific antibody therefrom; and,
   g. detecting said primate antibodies via the label.

9. A kit for the detection of primate antibodies in a biological sample that display immunological cross-reactivity towards $SIV_{cpz-ant}$ viral antigens comprising the following:

a. the viral lysate of claim 2, or one or more of the viral antigens of claims 3, 4, 5, or 6, attached to a solid support;
   b. control antigens which are not recognized by $SIV_{cpz-ant}$-specific antibodies;
   c. a positive antibody control consisting of $SIV_{cpz-ant}$-specific antibodies;
   d. a negative antibody control consisting of antibodies that do not react with $SIV_{cpz-ant}$-specific viral antigens;
   e. a labeled secondary antibody for the detection of antigen-antibody immune complexes; and
   f. appropriate buffers, substrates, and enzymes as required for detection of said antibodies.

* * * * *